United States Patent
Manson (10) Patent No.: US 10,815,549 B2
(45) Date of Patent: Oct. 27, 2020

(54) METHOD FOR THE PURIFICATION OF ALUMINA

(71) Applicant: AluChem Companies, Inc., Cincinnati, OH (US)

(72) Inventor: Ian Manson, Oakville (CA)

(73) Assignee: AluChem Companies, Inc., Cincinnati, OH (US)

( * ) Notice: Subject to any disclaimer, the term of this patent is extended or adjusted under 35 U.S.C. 154(b) by 82 days.

(21) Appl. No.: 16/177,652

(22) Filed: Nov. 1, 2018

(65) Prior Publication Data

US 2019/0070598 A1    Mar. 7, 2019

Related U.S. Application Data

(63) Continuation-in-part of application No. 15/284,585, filed on Oct. 4, 2016, now Pat. No. 10,144,650, which
(Continued)

(51) Int. Cl.
*C22B 7/00* (2006.01)
*C01G 23/047* (2006.01)
(Continued)

(52) U.S. Cl.
CPC ............ *C22B 7/009* (2013.01); *C01B 17/745* (2013.01); *C01C 1/028* (2013.01); *C01C 1/26* (2013.01);
(Continued)

(58) Field of Classification Search
CPC ....... C22B 7/009; C01C 1/028; C01C 51/412; C01B 17/745; C01F 7/765; C01F 7/004; C01G 23/0475
See application file for complete search history.

(56) References Cited

U.S. PATENT DOCUMENTS

| 2,849,289 A | 8/1958 | Zirngibl et al. |
| 8,728,437 B2 | 5/2014 | Stuart |

(Continued)

FOREIGN PATENT DOCUMENTS

| CN | 102560129 | * 7/2012 |
| CN | 103468978 A | 12/2013 |

OTHER PUBLICATIONS

Zhang, Haijun, et al. "Thermal Decomposition Kinetics of Ammonium Aluminum Carbonate Hydroxide." Key Engineering Materials, Trans Tech Publications, LTD, Feb. 11, www.scientific.net/KEM.368-372.1577.pdf. doi:10.4028/www.scientific.net/KEM.368-372.1577 (Year: 2008).*

(Continued)

*Primary Examiner* — Tima M. McGuthry-Banks
(74) *Attorney, Agent, or Firm* — Blank Rome LLP (57) ABSTRACT

Digestion of impure alumina with sulfuric acid dissolves all constituents except silica. Resulting sulfates, produced from contaminants in the impure alumina, remain in solution at approximately 90° C. Hot filtration separates silica. Solution flow over metallic iron reduces ferric sulfate to ferrous sulfate. Controlled ammonia addition promotes hydrolysis and precipitation of hydrated titania from titanyl sulfate that is removed by filtration. Addition of ammonium sulfate forms ferrous ammonium sulfate and ammonium aluminum sulfate solutions. Alum is preferentially separated by crystallization. Addition of ammonium bicarbonate to ammonium alum solution precipitates ammonium aluminum carbonate which may be heated to produce alumina, ammonia, and carbon dioxide. The remaining iron rich liquor also contains magnesium sulfate. Addition of oxalic acid generates insoluble ferrous oxalate which is thermally decomposed to ferrous oxide. Carbon monoxide reduces the ferrous oxide to metallic iron. Further oxalic acid addition
(Continued)

precipitates magnesium oxalate which is thermally decomposed to magnesium oxide.

21 Claims, 2 Drawing Sheets

Related U.S. Application Data is a continuation-in-part of application No. 14/255,791, filed on Apr. 17, 2014, now Pat. No. 9,458,522.

(51) Int. Cl.
| | |
|---|---|
| *C01F 5/06* | (2006.01) |
| *C01G 23/053* | (2006.01) |
| *C01C 1/02* | (2006.01) |
| *C01B 17/74* | (2006.01) |
| *C01F 7/76* | (2006.01) |
| *C01C 1/26* | (2006.01) |
| *C01F 7/00* | (2006.01) |
| *C07C 51/41* | (2006.01) |
| *B01D 9/00* | (2006.01) |

(52) U.S. Cl.
CPC ............... *C01F 5/06* (2013.01); *C01F 7/004* (2013.01); *C01F 7/765* (2013.01); *C01G 23/0475* (2013.01); *C01G 23/0532* (2013.01); *C07C 51/412* (2013.01); *B01D 2009/0086* (2013.01); *C01P 2006/80* (2013.01)

(56) References Cited

U.S. PATENT DOCUMENTS

| | | | |
|---|---|---|---|
| 9,458,522 B2 | 10/2016 | Manson | |
| 2004/0237719 A1* | 12/2004 | Becker | C01F 7/765 |
| | | | 75/586 |
| 2008/0124260 A1 | 5/2008 | Roche et al. | |
| 2012/0111150 A1* | 5/2012 | Marafi | C22B 7/007 |
| | | | 75/622 |
| 2017/0022069 A1 | 1/2017 | Manson | |

OTHER PUBLICATIONS

CN 102560129 Machine Translation (Year: 2012).*
Du et al. CN 103468978 A published Dec. 2013. Machine Translation.

* cited by examiner

METHOD FOR THE PURIFICATION OF ALUMINA

CROSS-REFERENCE TO RELATED APPLICATIONS

This application is a continuation-in-part of U.S. application Ser. No. 15/284,585 filed on Oct. 4, 2016, which issued as U.S. Pat. No. 10,144,650 on Dec. 8, 2014, which is a continuation-in-part of U.S. application Ser. No. 14/255, 791 filed on Apr. 17, 2014, which issued as U.S. Pat. No. 9,458,522 on Oct. 4, 2016.

STATEMENT REGARDING FEDERALLY SPONSORED RESEARCH OR DEVELOPMENT

Not Applicable

BACKGROUND OF THE INVENTION

1. Field of the Invention

The present invention generally relates to the purification of alumina. More particularly, it relates to the purification of alumina used as a catalyst or catalyst support.

2. Description of the Related Art Including Information Disclosed Under 37 CFR 1.97 and 1.98

Aluminum oxide is a chemical compound of aluminum and oxygen having the chemical formula $Al_2O_3$. It is the most commonly occurring of several aluminum oxides, and specifically identified as aluminum(III) oxide. It is commonly called alumina, and may also be called aloxide, aloxite, or alundum depending on particular forms or applications. It occurs naturally in its crystalline polymorphic phase $\alpha$-$Al_2O_3$ as the mineral corundum, varieties of which form ruby and sapphire. $Al_2O_3$ is significant in its use to produce aluminum metal, as an abrasive owing to its hardness, and as a refractory material owing to its high melting point The mineral corundum is natural aluminum oxide. Emery, ruby, and sapphire are impure crystalline varieties. The mixed mineral bauxite is a hydrated aluminum oxide. Bauxite ore is the main source for aluminum. Bauxite is a variety of laterite (residual sedimentary rock), and has no precise chemical formula. It is composed mainly of hydrated alumina minerals such as gibbsite [$Al(OH)_3$ or $Al_2O_3.3H_2O$)] in newer tropical deposits; in older subtropical, temperate deposits the major minerals are boehmite [$\gamma$-AlO(OH) or $Al_2O_3.H_2O$] and some diaspore [$\alpha$-AlO(OH) or $Al_2O_3.H_2O$]. The average chemical composition of bauxite, by weight, is 45 to 60% $Al_2O_3$ and 20 to 30% $Fe_2O_3$.

Laterites are soil types rich in iron and aluminum, formed in hot and wet tropical areas. Nearly all laterites are rust-red in color due to the presence of iron oxides. They develop by intensive and long-lasting weathering of the underlying parent rock. Tropical weathering (laterization) is a prolonged process of chemical weathering which produces a wide variety in the thickness, grade, chemistry and ore mineralogy of the resulting soils. The majority of the land area containing laterites is located in a band extending about 25 degrees north and south of the Equator.

Historically, laterite was cut into brick-like shapes and used in monument building. Since the mid-1970's, trial sections of bituminous-surfaced low-volume roads have used laterite in place of stone as a base course. Thick laterite layers are porous and slightly permeable and thus the layers may function as aquifers in rural areas. Locally available laterites are used in an acid solution, followed by precipitation to remove phosphorus and heavy metals at sewage treatment facilities.

Laterites are a source of aluminum ore. The ore exists largely in clay minerals and the hydroxides, gibbsite, boehmite, and diaspore, which resembles the composition of bauxite. In Northern Ireland, they once provided a major source of iron and aluminum ores. Laterite ores also were the early major source of nickel.

Iron contamination can be a problem with regard to alumina recovery through acid digestion of alumina-rich earths or laterites. Crystallization routes almost always result in iron inclusions.

In a process according to the present invention, iron conversion to the ferrous form minimizes iron inclusions. Additionally, conversion of all iron to the ferrous form allows iron separation by precipitation as an oxalate.

Separation may be complete and the iron chemically pure. Multiple crystallizations from an ammonium alum avoid caking and other problems occurring when simple ammonium sulfate is crystallized and calcined. During development of the invention, the principal challenges were chemistry-related in terms of testing the reactions and finding the correct range of chemicals, temperatures, pH etc. to make the process work.

In the past, laterite separations have not been of much interest as a process for obtaining alumina. The usual approach has been to search for pure alumina feeds where possible, with minimal iron as a contaminant.

Thus, bauxite feeds have been dissolved in caustic soda (the Bayer process) rejecting all iron as the hydroxide (red mud). In a process according to the present invention, value may be derived from all of the constituents of laterite.

The properties of aluminum oxide vary according to the method of preparation. It is commonly in the form of white powder, balls, or lumps of various mesh. It is noncombustible, has a density of 3.4-4.0, a melting point of 2030° C., is insoluble in water and difficultly soluble in mineral acids and strong alkali.

Aluminum oxide is used in the production of aluminum, the manufacture of abrasives, refractories, ceramics, electrical insulators, catalysts and catalyst supports, paper, spark plugs, crucibles and laboratory ware. It is also used as an adsorbent for gases and water vapors, chromatographic analysis, in fluxes, light bulbs, artificial gems and heat-resistant fibers, and also as a food additive (dispersing agent).

Activated alumina is a highly porous, granular form of aluminum oxide having preferential adsorptive capacity for moisture and odor contained in gases and some liquids. When saturated, it can be regenerated by heating. The cycle of adsorption and reactivation can be repeated many times. Granules of activated alumina range in size from powder (~7 microns for chromatographic work) to pieces approximately 1½ inches in diameter. It has an average density of approximately 50 lb/ft$^3$.

Activated alumina is used as a desiccant for gases and vapors in the petroleum industry. It is also used as a catalyst or catalyst carrier, in chromatography, and in water purification.

Aluminum oxide catalyzes a variety of reactions used in the chemical industry. In its largest scale application, aluminum oxide is the catalyst in the Claus process for converting hydrogen sulfide waste gases into elemental sulfur in refineries. It is also useful for the dehydration of alcohols to alkenes.

Aluminum oxide serves as a catalyst support for many industrial catalysts, such as those used in hydrodesulphurization and some Ziegler-Natta polymerizations.

Iron contamination can be a problem with regard to alumina purification through acid digestion. Crystallization routes almost always result in iron inclusions.

In a process according to the present invention, iron conversion to the ferrous form minimizes iron inclusions. Additionally, conversion of all iron to the ferrous form allows iron separation by precipitation as an oxalate.

Separation may be complete and the iron chemically pure. Multiple crystallizations from an ammonium alum avoid caking and other problems occurring when simple ammonium sulfate is crystallized and calcined. During development of the invention, the principal challenges were chemistry-related in terms of testing the reactions and finding the correct range of chemicals, temperatures, pH etc. to make the process work.

BRIEF SUMMARY OF THE INVENTION

The acid digestion of impure alumina with sulfuric acid is used to dissolve all constituents except silica. The sulfates resulting from the digestion—aluminum sulfate, along with ferric sulfate, titanyl sulfate, and magnesium sulfate for alumina contaminated with iron-, titanium-, and/or magnesium-containing species—remain in solution at approximately 90° C.

Hot filtration separates silica and any calcium content from the solution.

Solution flow over metallic iron reduces ferric sulfate to ferrous sulfate.

Controlled ammonia addition promotes hydrolysis and precipitation of hydrated titania from titanyl sulfate. This may be removed by hot filtration. Sulfuric acid is a byproduct.

Continued addition of ammonia (as ammonium sulfate) forms ferrous ammonium sulfate and ammonium aluminum sulfate solutions. The steep solubility curve of ammonium alum allows preferential separation by crystallization. Multiple crystallizations refine to extremely pure ammonium alum. Ammonia addition to ammonium alum solution precipitates aluminum hydroxide as a primary product, leaving ammonium sulfate in solution. In an alternative embodiment, alumina is produced via the conversion of aluminum sulfate to ammonium aluminum carbonate. The ammonium aluminum carbonate product contains approximately 36.5% alumina and has no water of crystallization. This dry solid readily and rapidly decomposes between temperatures of about 90° C. and about 265° C. to liberate carbon dioxide, water vapor and ammonia as the temperature is increased.

The remaining iron rich liquor may be adjusted to equimolar conditions with ammonia. This solution also contains magnesium sulfate. The addition of oxalic acid generates insoluble ferrous oxalate as the second major product. This may be filtered and washed. Sulfuric acid and ammonium sulfate solution are by-products.

The ferrous oxalate may be thermally decomposed to ferrous oxide and carbon monoxide. The carbon monoxide may be subsequently used to reduce the ferrous oxide to metallic iron.

Further oxalic acid addition to the process liquor precipitates magnesium oxalate leaving sulfuric acid by-product. The magnesium oxalate is thermally decomposed to magnesium oxide.

Ammonia may be added to neutralize all sulfuric acid generated in the various process stages and may be combined with directly produced ammonium sulfate streams. The alum solution may be sold as is, or crystallized to dry product for sale. Alternatively, alum crystals may be thermally decomposed to sulfuric acid and ammonia and recycled in the process.

DETAILED DESCRIPTION OF THE INVENTION

The invention may best be understood by reference to the exemplary embodiment(s) described below.

It has been found that acid digestion of impure alumina with sulfuric acid may be used to dissolve all substances present except silica. Aluminum sulfate, ferric sulfate, titanyl sulfate, and magnesium sulfate remain in solution at approximately 90° C.

Hot filtration separates silica and any calcium content from the solution.

Solution flow over metallic iron reduces ferric sulfate to ferrous sulfate.

Controlled ammonia addition promotes hydrolysis and precipitation of hydrated titania from titanyl sulfate. This may be removed by hot filtration. Sulfuric acid is a byproduct.

Continued ammonia addition as sulfate forms ferrous ammonium sulfate and ammonium aluminum sulfate solutions. Ammonium aluminum sulfate, also known as ammonium alum or just alum, is a white crystalline double sulfate usually encountered as the dodecahydrate, formula $(NH_4)Al(SO_4)_2 \cdot 12H_2O$. The steep solubility curve of ammonium alum allows preferential separation by crystallization. Multiple crystallizations refine to extremely pure ammonium alum. Ammonia addition to ammonium alum solution precipitates aluminum hydroxide as a primary product, leaving ammonium sulfate in solution.

The remaining iron rich liquor may be adjusted to equimolar conditions with ammonia. The solution also contains magnesium sulfate. Addition of oxalic acid generates insoluble ferrous oxalate as the second major product. This may be filtered and washed.

Sulfuric acid and ammonium sulfate solution are by-products. Ferrous oxalate may be thermally decomposed to ferrous oxide and carbon monoxide. Carbon monoxide may be subsequently used to reduce the ferrous oxide to metallic iron.

Further oxalic acid addition to the process liquor precipitates magnesium oxalate leaving sulfuric acid by-product. Magnesium oxalate may be thermally decomposed to magnesium oxide.

Ammonia may be added to neutralize all sulfuric acid generated in the various process stages and may be combined with directly produced ammonium sulfate streams. The alum solution may be sold as is, or crystallized to dry product for sale. Alternatively, alum crystals may be decomposed to sulfuric acid and ammonia for recycle to process.

Process Feed Material

For one particular laterite from India, the chemical analysis was as follows:

| Component | Weight % | 1000 kg as mined |
|---|---|---|
| $Al_2O_3$ | 52.18 | 401.8 kg |
| $TiO_2$ | 3.57 | 27.5 kg |
| $Fe_2O_3$ | 39.29 | 302.5 kg |
| $SiO_2$ | 3.97 | 30.6 kg |
| MgO | 1.00 | 7.7 kg |
| Totals | 100.01% | 230.0 kg moisture |

Process Mass Balance
Digestion $$Al_2O_3 + 3H_2SO_4 + SiO_2 \rightarrow Al_2(SO_4)_3 + 3H_2O + SiO_2$$

$$TiO_2 + H_2SO_4 \rightarrow TiOSO_4 + H_2O$$

$$Fe_2O_3 + 3H_2SO_4 \rightarrow Fe_2(SO_4)_3 + 3H_2O$$

$$MgO + H_2SO_4 \rightarrow MgSO_4 + H_2O$$

Example 1

The 401.8 kilograms of aluminum oxide from the 1000-kg laterite ore sample may be digested by 1159.5 kilograms of sulfuric acid to produce 1348.3 kilograms of aluminum sulfate and 213.0 kilograms of water. The 30.6 kilograms of silica in the ore sample will remain undigested and may be separated by hot filtration.

The 27.5 kilograms of titanium dioxide from the 1000-kg laterite ore sample may be digested by 33.8 kilograms of sulfuric acid to produce 55.07 kilograms of titanium sulfate and 6.2 kilograms of water.

The 302.5 kilograms of ferric oxide from the 1000-kg laterite ore sample may be digested by 557.4 kilograms of sulfuric acid to produce 757.5 kilograms of ferric sulfate and 102.4 kilograms of water.

The 7.7 kilograms of magnesium oxide from the 1000-kg laterite ore sample may be digested by 18.7 kilograms of sulfuric acid to produce 23.0 kilograms of magnesium sulfate and 3.4 kilograms of water.

Note Regarding Iron Digestion

Iron separation from alumina in a process according to the invention depends upon the iron being in the ferrous form. Iron in alumina samples is usually present as ferric oxide (the hæmatite form of $Fe_2O_3$).

There is a small possibility that goethite FeO(OH) may also be present but acid digestion will produce a bulk of the ferric form of sulfate. This may be converted to ferrous sulfate by passing the hot digestion liquor through a bed of steel. This should be good quality scrap steel to minimize the introduction of impurities. The final stage of digestion prior to component separations thus may be the passage of the digestion liquor over iron. All ferric iron must be converted, so testing is critical.

$$Fe_2(SO_4)_3 + Fe \rightarrow 3FeSO_4$$

Example 2

The 757.5 kilograms of ferric sulfate produced in Example 1 may be passed through a bed of [scrap] steel where they may be reduced to 863.3 kilograms of ferrous sulfate while consuming 105.8 kilograms of iron.

Standard testing for the presence of ferric ions involves the use of potassium ferricyanide. Any $Fe^{+3}$ ions will give a brown coloration but no precipitate. $Fe^{+2}$ forms a dark blue precipitate (Turnbull's blue). Potassium thiocyanate gives a deep red coloration to solutions with $Fe^{+3}$.

Aluminum Oxide

Ammonium sulfate addition to the digestion liquor forms both ammonium aluminum sulfate and ferrous ammonium sulfate. Solution cooling crystallizes the ammonium alum double salt while leaving the ferrous liquor in solution.

$$Al_2(SO_4)_3 + (NH_4)_2SO_4 + 24H_2O \rightarrow 2(NH_4Al(SO_4)_2 \cdot 12H_2O)$$

Example 3

The 1348.3 kilograms of aluminum sulfate from Example 1 may be reacted with 520.7 kilograms of ammonium sulfate and 1703.8 kilograms of water to produce 1869.1 kilograms of the ammonium alum double salt together with 1703.8 kilograms of water of hydration.

Multiple crystallizations may be effected to purify the crystal product.

Ammonia addition to the purified salt solution precipitates aluminum hydroxide.

$$NH_4Al(SO_4)_2 + 3NH_3 + 3H_2O \rightarrow Al(OH)_3 + 2(NH_4)_2SO_4$$

Example 4

The 1869.1 kilograms of the ammonium alum double salt from Example 3 may be reacted with 402.7 kilograms of ammonia and 426.0 kilograms of water to produce 614.8 kilograms of aluminum hydroxide and 2082.9 kilograms of ammonium sulfate.

Temperature, agitation speed, and rate of ammonia addition (as gas or hydroxide) have been found to affect the form of aluminum hydroxide precipitated. The precipitate may be washed, dried, and calcined to gamma alumina.

$$2Al(OH)_3 \rightarrow Al_2O_3 + 3H_2O$$

Example 5

The 614.8 kilograms of aluminum hydroxide from Example 4 may be calcined to produce 401.8 kilograms of alumina while liberating 213.0 kilograms of water.

The remaining digestion liquor will contain iron, and magnesium as sulfates, and ferrous ammonium sulfate.

Iron

Ammonia and/or ammonium sulfate additions may be made to the digestion liquor to provide equimolar ratios of ammonia and sulfate needed for the iron double salt precursor. Ammonium ion maintains a slightly acidic condition and inhibits ferrous conversion to ferric iron, particularly with a slight excess of sulfuric acid in solution.

$$FeSO_4 + (NH_4)_2SO_4 \rightarrow (NH_4)_2Fe(SO_4)_2$$

Example 6

The 863.3 kilograms of ferrous sulfate from Example 2 may be reacted with 751.0 kilograms of ammonium sulfate to produce 1614.3 kilograms of ferrous ammonium sulfate.

Oxalic acid may then be added to form insoluble ferrous oxalate.

$$(NH_4)_2Fe(SO_4)_2 + H_2C_2O_4 \cdot 2H_2O \rightarrow FeC_2O_4 \cdot 2H_2O + H_2SO_4 + (NH_4)_2SO_4$$

Example 7

The 1614.3 kilograms of ferrous ammonium sulfate from Example 6 may be reacted with 716.5 kilograms of oxalic acid to produce 817.9 kilograms of ferrous oxalate (with 204.8 kilograms of water of hydration), 557.4 kilograms of sulfuric acid and 751.0 kilograms of ammonium sulfate.

The pure salt obtained after washing may be dried and heated to decompose the oxalate.

$$FeC_2O_4 \cdot 2H_2O \rightarrow FeO + CO + CO_2 + 2H_2O$$

Example 8

The 817.9 kilograms of ferrous oxalate (containing 204.8 kilograms of water of hydration) may be decomposed by heating to yield 408.3 kilograms of ferrous oxide, 159.2 kilograms of carbon monoxide, 250.1 kilograms of carbon dioxide, and 204.8 kilograms of water.

The ferrous oxide produced was finely divided and chemically active and must be reduced to metallic iron. Carbon monoxide released from the oxalate decomposition may be stored for subsequent use as a reducing agent to convert the iron oxide to iron.

$$FeO + CO \rightarrow Fe + CO_2$$

Example 9

The 408.3 kilograms of ferrous oxide from Example 8 may be reduced with 159.2 kilograms of carbon monoxide to yield 317.4 kilograms of metallic iron and 250.1 kilograms of carbon dioxide.

The fine particulate iron produced by the process is pyrophoric and should preferably be briquetted under an inert atmosphere before packaging for sale.

Magnesium Oxide

Solubility product data for iron and magnesium oxalates indicates that ferrous oxalate will precipitate before magnesium oxalate. Oxalic acid addition to the digestion liquor after iron removal may be used to precipitate the magnesium content:

$$MgSO_4 + H_2C_2O_4 \cdot 2H_2O \rightarrow MgC_2O_4 \cdot 2H_2O + H_2SO_4$$

Example 10

The 23.0 kilograms of magnesium sulfate in the digestion liquor of Example 1 may be treated with 24.1 kilograms of oxalic acid to precipitate 28.3 kilograms of magnesium oxalate while forming 18.7 kilograms of sulfuric acid.

The magnesium oxalate may be filtered, washed, dried and heated to decompose the oxalate and produce chemical grade active magnesia.

$$MgC_2O_4 \cdot 2H_2O \rightarrow MgO + CO + CO_2 + 2H_2O$$

Example 11

The 28.3 kilograms of magnesium oxalate from Example 10 may be heated to provide 7.7 kilograms of magnesia while liberating 5.3 kilograms of carbon monoxide, 8.4 kilograms of carbon dioxide and 6.9 kilograms of water.

Ammonium Sulfate

The ammonium sulfate produced in the processing is in the form of a solution that may be crystallized. The crystals may be sold as product or decomposed to sulfuric acid and ammonia.

$$(NH_4)_2SO_4 \rightarrow H_2SO_4 + NH_3$$

By way of example, the above-described process when applied to a 1000-kilogram batch of laterite will produce 1562.2 kilograms of ammonium sulfate which may be decomposed to 1159.5 kilograms of sulfuric acid and 402.7 kilograms of ammonia.

The decomposition reaction involves heating ammonium sulfate crystals in hot concentrated sulfuric acid, and has been described previously.

The quantities of acid and ammonia produced match the process requirements for digestion and crystallization exactly. Such 100 percent efficiency may not be practical but would assure minimum make-up requirements.

Chemical consumption and production figures for one particular process according to the invention are as follows:

Consumption

| Material | Quantity (in kilograms) |
|---|---|
| mined laterite | 1000 (770.0 kg oxide solids combined with 230.0 kg water) |
| sulfuric acid | 1159.5 |
| ammonia | 402.7 |
| scrap iron | 105.8 |
| oxalic acid | 740.6 |

Production

| Material | Quantity (in kilograms) |
|---|---|
| aluminum oxide | 401.8 |
| iron | 317.4 |
| silica | 30.6 |
| titanium dioxide | 27.5 |
| magnesium oxide | 7.7 |
| ammonium sulfate | 1562.2 (1159.5 kg sulfuric acid and 402.7 kg ammonia) |
| carbon monoxide | 5.3 (plus 159.2 kg from ferrous oxalate decomposition) |
| carbon dioxide | 508.6 (net, assuming use of 159.2 kg CO for iron reduction) |

Chemical consumption and production figures for one particular process according to the invention producing 1000 tonnes of alumina are as follows: (Note: as used herein, 1 tonne=1 metric ton=1,000,000 grams)

Consumption

| Material | Quantity (in tonnes) |
|---|---|
| laterite | 2489 |
| sulfuric acid | 2886 |
| ammonia | 1002 |
| scrap iron | 263 |
| oxalic acid | 1843 |

Production

| Material | Quantity (in tonnes) |
|---|---|
| alumina | 1000 |
| iron | 790 |
| silica | 76 |
| titania | 68 |
| magnesia | 19 |
| ammonium sulfate | 3888 |
| carbon monoxide | 13 |
| carbon dioxide | 1266 |

Note that the carbon dioxide produced is about 1.3 times the weight of laterite mined. More specifically, carbon dioxide production is 2.4 times the weight of iron content recoverable from mined material. Carbon dioxide is released by the decomposition of oxalates, and these may be sourced from oxalic acid. Oxalic acid may be manufactured using several chemical routes. The simplest, and oldest, chemical process involves the oxidation of carbohydrates using nitric acid. Sugars are decomposed to oxalic acid, and nitric acid decomposed to oxides of nitrogen. The oxides of nitrogen are absorbed in water to prepare fresh nitric acid for theoretical 100 percent acid recycle. The process is described in more detail below. Sugars are produced from plant material, directly as sugar, or via hydrolysis of plant starches. These natural feed materials grow using photosynthesis of carbon dioxide present in the atmosphere. This carbon dioxide may be returned to atmosphere when the oxalates decompose. Provided that sugar sourced oxalic acid is used, then the process is "green" or carbon neutral, and not a contributor to global warming.

Oxalic Acid

Oxalic acid may be used to convert all of the iron content in the laterite to pure iron. Scrap steel equal to half the weight of laterite iron may be used for the ferric to ferrous conversion and may be itself converted to pure iron. Iron manufactured using the process could be partially recycled for the ferric conversion, but scrap use may be preferable economically because it increases iron production by 50 percent for the same oxalic acid consumption. Oxalic acid is then a process critical chemical and consumed at a rate of approximately 3.5 times the weight of iron recoverable from the laterite.

Oxalic acid availability may be important and it may be worth considering on-site production. Proximity to agricultural cellulosic waste or refined sugar waste, or to sugar itself would allow relatively low cost oxalic acid manufacture. The sugar process may be the least expensive to implement for small scale production.

Starches consist of chains of glucose molecules, easily broken apart by acid hydrolysis (sulfuric acid and/or oxalic acid) into separate glucose molecules. The monosaccharides glucose and fructose are the preferred precursor for oxalic acid manufacture. Low-cost agricultural waste can be converted to glucose through acid digestion. The process may be simple or more complicated depending upon the means required to disrupt the waste materials (grinding, steam explosion etc.) prior to hydrolysis.

Conversion to oxalic acid may then proceed as follows:

$$4C_6H_{12}O_6+18HNO_3+3H_2O \rightarrow 12(COOH)_2.2H_2O+9N_2O$$

$$C_6H_{12}O_6+12HNO_3 \rightarrow 3(COOH)_2.2H_2O+3H_2O+3NO+9NO_2$$

Refined sucrose (as pure material through low-grade molasses) may be hydrolyzed to provide a good feed material for the manufacture of oxalic acid Equation balances show one unit of glucose producing 2.1 units of oxalic acid crystals. Processing and reaction inefficiencies may reduce the yield to, at worst, about 1.9 units of oxalic acid per unit of glucose feed. Vanadium pentoxide and ferric iron catalyze the reaction, which may be conducted in 50% sulfuric acid. Oxalic acid may be crystallized and the catalyzed mother liquor returned to the digestion stage.

Oxalic acid at 2027 tonnes (10% more than theoretical weight for 1000 tonnes of alumina made from Indian laterite) requires a glucose feed of 965 tonnes.

Nitric Acid Manufacture

The oxalic acid reaction was often conducted in less-developed countries at atmospheric pressure to maximize acid yield. It has been found that pressurized reactions, without air admission, maintain good conversions and offer the benefit of high pressure nitrogen oxides gas release. The oxides of nitrogen are themselves oxidized to nitrogen dioxide before absorption in water to form nitric acid. The reaction is self-pressurizing, through gas release, as the stirred reaction autoclave is heated to about 70° C. and nitric acid added gradually over 4 to 5 hours. High pressure oxides from the autoclave remove the need for expensive gas pressurization equipment and reduce the size and cost of a nitric acid plant considerably.

Temperature rises to about 75° C. in the course of the reaction and pressure may be held at about 150 p.s.i.g. This is a good combination for the gas feed to a nitric acid plant.

The generic equation for nitric acid need for the oxalic acid process is as follows.

$$C_6H_{12}O_6+6HNO_3 \rightarrow 3(COOH)_2.2H_2O+6NO$$

2025 tonnes of nitric acid may be used to oxidize 965 tonnes of glucose to 2026 tonnes of oxalic acid. 964 tonnes of NO should be generated. The NO may be oxidized to $NO_2$ in a nitric acid plant and absorbed in water. Secondary NO may be re-oxidized. Recycle efficiency can be very high. Dinitrogen tetroxide (nitrogen tetroxide) is the chemical compound $N_2O_4$. It forms an equilibrium mixture with nitrogen dioxide. Some call this mixture "dinitrogen tetroxide," while others call it "nitrogen dioxide."

$$2NO+O_2 \rightarrow 2NO_2 \leftrightarrows N_2O_4$$

964 tonnes of NO would require 514 tonnes of oxygen for conversion to 1478 tonnes of nitrogen dioxide.

$$3NO_2+H_2O \rightarrow 2HNO_3+NO \quad \text{(Stage 1)}$$

1478 tonnes of nitrogen dioxide would react with 193 tonnes of water to yield 1350 tonnes of nitric acid and 321 tonnes of nitric oxide.

The nitric oxide from Stage 1 may be returned for re-oxidation and recycle as $NO_2$ to the absorber.

Alternative Method Using a Carbonate Route

The process disclosed above involves the acid digestion of aluminous materials to form sulfate solutions. Often, the digestion liquor contains unwanted impurities such as titanium, magnesium and iron remaining as sulfates in solution. In the process disclosed above, isolation of the alumina content of the liquor is via aluminum sulfate conversion to ammonium aluminum sulfate. This double salt crystallizes with great ease. Very pure ammonium alum crystals may be obtained by this process provided the crystals are small and any iron in the mother liquor is in the ferrous form, $$Al_2(SO_4)_3.nH_2O+(NH_4)_2SO_4 \rightarrow (NH_4)_2Al_2(SO_4)_4.24H_2O+(n-24)H_2O$$

Iron conversion to the ferrous form reduces the likelihood of iron co-crystallization or surface adhesion to the ammonium alum crystals. Additionally, the generation of small crystals reduces the likelihood of mother liquor inclusions. Testing has shown that multiple crystallizations provide an ammonium alum of extremely high purity. A Swenson draft tube baffle (DTB) crystallizer (Swenson Technology, Inc., 26000 Whiting Way, Monee, Ill. 60449-8060 USA) may be designed for bulk production of a crystal of the desired small size. Chemical techniques may be used to recover the iron content of bauxite-based digestion liquors together with separations and recovery of the other elements present. Low-iron bauxites, alum inas, or alums may also be used as feeds to the process to reduce the number of purification steps.

Process Development

The sophistication and expense of multiple Swenson DTB crystallizers in the process may be overcome to a large extent by using chilled crystallization tanks. Cooling may be effected through the crystallizer walls or through slack internal tubing. Only small crystals develop (provided that agitation rates are high) which minimizes liquor inclusions. Excess ammonium sulfate additions (25% to 30% above stoichiometric) encourage complete conversion of aluminum sulfate to ammonium alum. Complete conversion is desirable to ensure single specie crystallizations and rejection of impurities by the newly formed crystals. Crystal washing with ammonium sulfate solution may further reduce impurity levels at the crystal surfaces and maintains the integrity of the ammonium alum solids formed. Second or third crystallizations may be accomplished with little additional energy expense, provided heat pumps transfer recovered cooling energy into the heat needed to re-dissolve the crystal crop between each stage. This is a less expensive option than the evaporative cooling and interstage compressors needed with the small temperature driving force Swenson DTB crystallizers. Crystallizer size may also be greatly reduced using the direct chill process with its large temperature driving force. Chilled crystallizer sizes are linked to the chilling surface and agitation intensity. Continuous crystallization using tanks in series or parallel may be used.

Pre-crystallization treatment of hot ammonium alum liquor with complexing agents such as salicylic acid and EDTA may be used to bind metallic impurities such as iron, copper, nickel, etc., as soluble entities. Dosing at 35% excess above contaminating metal ion stoichiometry has been found to provide substantially complete impurity capture. Ammonium alum solutions do not form ligands with these agents and the impurities remain as soluble complexes and do not co-crystallize. Polishing filtration of the hot liquor may be used to remove solid impurities that could act as crystal seeds and introduce crystal contamination. Clean crystallization of ammonium alum may follow and crystal washing may substantially remove surface contamination. Complexing agents may be retained in the ammonium sulfate product solution. Ferric iron conversion and single crystallization may form sufficiently pure ammonium alum.

Ammonium Alum Processing to Alumina

Ammonium alum may be decomposed directly to alumina. However, the decomposition may be unsatisfactory because the crystals melt in their own water of crystallization and cake on hot contact surfaces. High temperatures are needed to separate the ammonia and sulfur oxides, and recovery for regeneration can be difficult. Ammonium alum contains approximately 10.9% alumina. Thus, direct heating to decomposition can be wasteful of energy. The product is a gamma form of alumina.

Alternatively, the ammonium alum may be neutralized with ammonia to precipitate aluminum hydroxide. The neutralization is relatively easy to complete but correct precipitation conditions must be present to minimize gel formation and allow subsequent filter cake washing. It has been found that the neutralization procedure is sensitive and errors are unforgiving if unmanageable gel formation occurs.

$$NH_4Al(SO_4)_2+3NH_3+3H_2O \rightarrow Al(OH)_3+2(NH_4)_2SO_4$$

The product is obtained in a pseudoboehmite form which may be easily converted to gamma alumina.

Preferred Process for Ammonium Alum Conversion to Alumina

It has been discovered that certain difficulties with the above processes may be overcome by converting the ammonium alum to basic ammonium aluminum carbonate. This is achieved by the reaction of the ammonium alum with ammonium bicarbonate:

$$(NH_4)_2Al_2(SO_4)_4 \cdot 24H_2O + 8NH_4HCO_3 + nH_2O \rightarrow (NH_4)_2Al_2CO_3(OH)_2 + 4(NH_4)_2SO_4 + (n+24)H_2O + 7CO_2\uparrow + NH_3\uparrow$$

The reaction is strongly endothermic and is preferably conducted with a small excess of ammonium sulfate in the starting solution in order to maintain the composition of the ammonium alum as it is converted to carbonate. Tank heating may be used to maintain a constant reaction temperature. Ammonium bicarbonate may be used at 25% above the stoichiometric requirement to drive the reaction to completion.

This sequence of chemical addition is preferred in order to avoid the formation of ammonium aluminate $NH_4AlO_2$. The ammonium bicarbonate solution may be prepared as a first step using strong agitation and at a temperature of about 40° C. to avoid decomposition. Crystals of ammonium alum may then added at a controlled rate and the suspension left to ripen for about 30 minutes. A fine carbonate precipitate is formed and the settling rate may be increased using a flocculating aid. The floc settles quickly, allowing decantation to be used prior to simple filtration and water washing steps.

The ammonium aluminum carbonate product contains approximately 36.5% alumina and has no water of crystallization. This dry solid readily and rapidly decomposes at temperatures between about 90° C. and 265° C. to liberate carbon dioxide, water vapor, and ammonia as the temperature is increased.

$$(NH_4)_2Al_2CO_3(OH)_2 \rightarrow Al_2O_3 + NH_3\uparrow + CO_2\uparrow + H_2O\uparrow$$

Calcination following a gradual temperature ramp may provide substantially complete carbonate decomposition at a temperature of about 400° C. The reactive powder product is an amorphous phase alumina. A more rapid calcination regime may cause secondary ammonium aluminate formation. This may require a temperature soak at about 500° C. to effect complete carbonate decomposition and generate high-surface, gamma phase alumina as the powder product.

The ammonia and carbon dioxide released during the reaction and carbonate decomposition steps may be recycled and reacted with water to form ammonium bicarbonate.

Ammonium aluminum carbonate has a lower decomposition temperature and three times the alumina content of ammonium alum. Moreover, the decomposition products may easily be recycled in the process. For these reasons, this process may be more advantageous than that disclosed in U.S. Pat. No. 9,458,522 the contents of which are hereby incorporated by reference in their entirety.

Alumina made from this process may be simply reacted with sulfuric acid to make paper grade alum, heated to form catalytic grade high-surface aluminas, or heated further to form high-purity alpha alumina. Complexing additives may allow extremely high purity aluminas to be made that are suitable for synthetic sapphire production.

A secondary use for the alumina product may be as a feed for synthetic cryolite manufacture. The alumina formed is very reactive.

Figure 1:
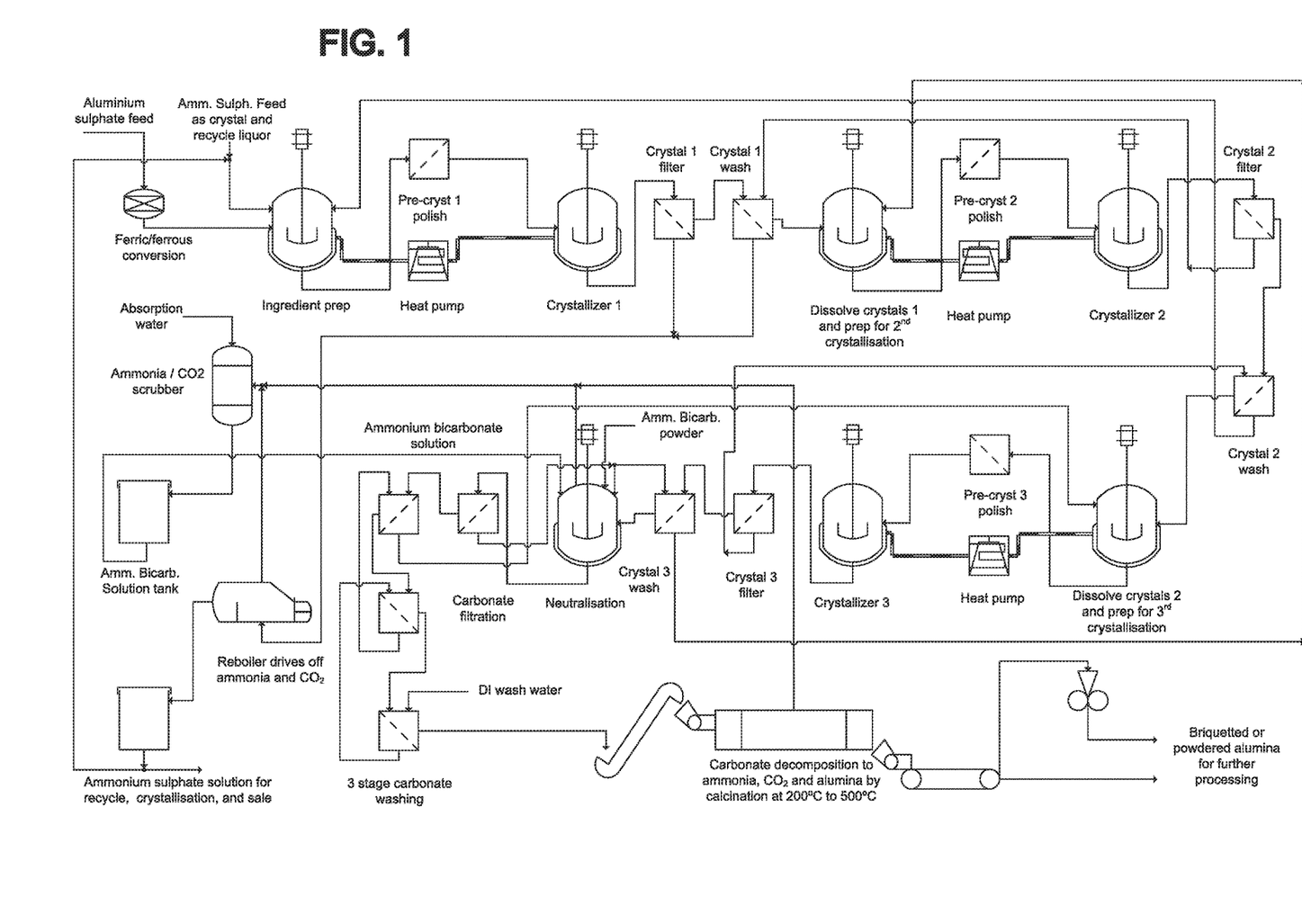
FIG. 1 is a schematic diagram of a process according to the invention for alumina production via the conversion of aluminum sulfate to ammonium aluminum carbonate.
Figure 2:
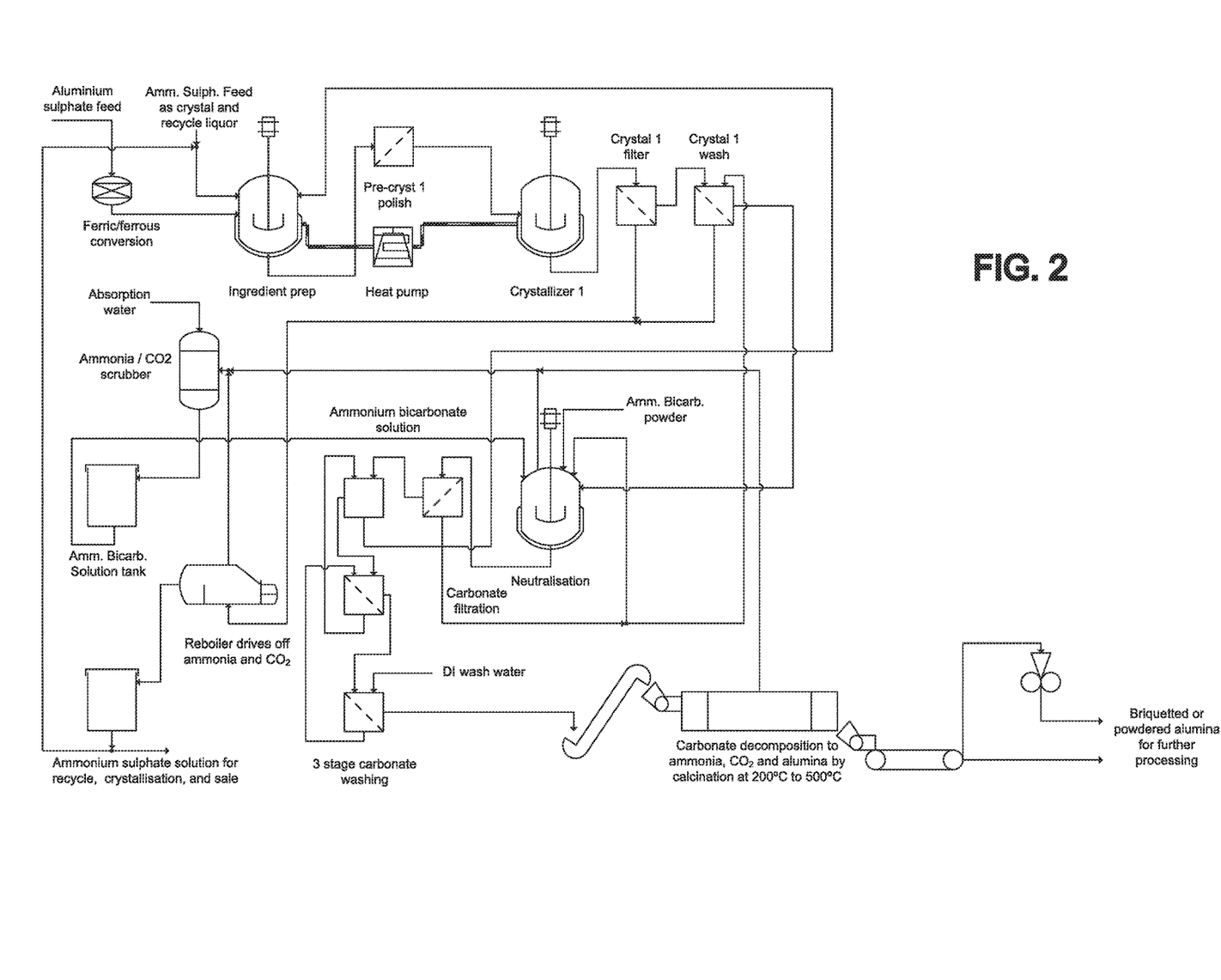
FIG. 2 is a schematic diagram of a process according to the invention for alumina production via the conversion of aluminum sulfate to ammonium aluminum carbonate that has a single crystallization step.

This alternative process is illustrated schematically in FIGS. 1 and 2.

The impurity levels in feed chemicals may be large or small and chemical analysis may be used to decide the best purification route to follow. Usually, iron is the principal impurity in aluminum sulfate feed. Its effect upon ammonium alum crystallization may be minimized by conversion of the ferric form to the ferrous form. Such conversion is inexpensive if the sulfate liquor is passed over metallic iron. A single crystallization after such treatment may be sufficient to provide clean crystals to be used for carbonate conversion. Any residual impurities may require second and even third crystallization steps to improve crystal purity. Impurity removal may be effected by the use of complexing agents to bind unwanted cations. Salicylic acid is effective mainly with divalent metal cations and will minimize co-crystallization of Ca, Mg, Cu, Ni etc., with the ammonium alum. Monovalent sodium and potassium cations may be more readily isolated using EDTA.

Crystallization Stages

The steep solubility curve for ammonium alum crystallization indicates that rapid and vigorous crystallization will occur unless cooling is well controlled. During development of the process, fine solids contamination of crystallization liquors initially caused significant problems because of early crystal formation through false seeding. This resulted in crystal inclusions of mother liquor in addition to the seed impurity contamination. It was found that these problems could be eliminated by hot filtration of the liquor prior to cooling with good agitation of the cooling crystal and mother liquor magma. Crystal formation was well controlled and uniform small crystals were obtained.

Laboratory mixing temperatures for the feed ingredients were finalized at 80° C. followed by solution cooling at approximately 1.4° C. per minute to generate a crystal crop. Crystals were re-dissolved for second and third stage crystallizations using the same conditions.

Carbonate Reaction

Experimental work has shown that rapid combination of ammonium bicarbonate and ammonium aluminum sulfate solutions may cause severe unwanted precipitation and aluminum conversion to both hydroxide and carbonate forms rather than the carbonate exclusively. Any hydroxide gel product formed remains stable and will not react back to the carbonate. It is contemplated that severe concentration gradients between reactants cause this problem and the lack of uniform reaction zone homogeneity cannot be overcome if only solution mixing is followed. Applicant has overcome this problem with intense mixing of the bicarbonate solution prior to and during the gradual addition of ammonium alum crystals. It is contemplated that each crystal is then in an individual reaction zone and reacts as it dissolves. Addition and reaction time combinations up to 90 minutes have resulted in complete reaction with no hydroxide formation.

Heating of the reaction mix to maintain a temperature of 40° C. has proven successful. Precipitate ripening of up to 30 minutes allowed all carbonate product to stabilize. The very fine precipitate was slow to settle independently but settled very well to a dense sludge. Settling took up to two hours for the finest precipitate particles but decantation was effective in concentrating the sludge prior to filtration and washing stages. Anionic polyacrylamide flocculant, added to the suspended precipitate mix at a concentration of 0.25%, caused rapid floc formation with complete settling occurring in only 17 minutes. Washing and multiple decantations left a clean sludge and were uncomplicated.

Carbonate Conversion to Oxide

Carbonate sludge dried at 100° C. for 2 hours produced a fine white powder. This powder was then heated for a further 3 hours using a uniform temperature ramp to 400° C.

Catalyst Recovery

In another embodiment of the invention, a contaminated alumina catalyst or a contaminated alumina-supported catalyst can be recovered and recycled by first separating the catalyst into a lower density portion and a higher density portion. The higher density portion may be treated for recovery of metals and alumina purification while the lower density portion may be returned to the process as still-active catalyst.

An exemplary process according to this embodiment of the invention is a process for recovering reusable spent catalyst from VGO and residuum hydroprocessing operations. Petroleum and bitumen refiners consume large quantities of hydroprocessing catalyst every year in processing heavy feedstocks such as vacuum gas oil (VGO) and residuum ("resid"). One of the primary deactivators of these catalysts is vanadium. The vanadium is present in the heavy feedstocks and is deposited on the catalyst. However, the catalyst unloaded from these reactors typically has a broad range of vanadium levels. In the case of ebullated bed units, as much as 25% may have been in use for 10 days or less, and the remaining 75% of the catalyst may have been in service from 11 days up to several years. In the case of fixed bed catalyst reactors, the vanadium loading may be as high as 20% on the top of the reactor and below 1 at the bottom of the reactor. Many of these reactors are dumped through a nozzle on the bottom of the reactor which causes intermixing of the high, medium, and low vanadium contaminated spent catalyst.

Various processes have been proposed for processing these spent catalysts for reuse. Some involve regeneration and/or rejuvenation of the spent catalyst in combination with density separation. This embodiment of the invention combines stripping and density separation on the spent catalyst that is returned for reuse and the recovery of alumina. The primary benefits of this approach are: 1) fewer steps and less costly processing of the spent catalyst prior to its reuse; 2) preservation of the catalyst metals in their sulfided form (which is their active form in the hydroprocessing operation); and 3) the recovery of reusable alumina.

The purpose of this embodiment of the invention is to segregate mildly spent catalyst from highly spent catalyst for VGO and resid hydroprocessing operations so that the mildly spent catalyst can be reused with minimal processing steps. Another benefit of this invention is that the vanadium removed from the VGO and resid hydroprocessing operations is concentrated on less spent catalyst volume, which in turn facilitates the recovery of vanadium for use in other industries.

Spent catalyst from a VGO or residuum hydroprocessing operation may be stripped of surface hydrocarbons at least to the extent required to render it non-tacky and free-flowing. The stripped catalyst may then be subjected to a segregation process to separate the mildly spent catalyst (which has a lower particle density due to a lower vanadium content) from the highly spent catalyst (which has a higher particle density due to a higher vanadium content). The mildly spent catalyst may be reused directly in the VGO or resid hydroprocessing operation. The highly spent catalyst may be sent to a metal reclamation operation. The higher concentration of vanadium on this highly spent catalyst facilitates the recovery of vanadium.

This embodiment of the invention may be applied to spent catalyst from the hydrotreating of the heavier fractions of petroleum or bitumen from oil sands deposits.

The first step may be to strip surface hydrocarbons from the spent catalyst to the degree necessary to make the spent catalyst free-flowing and therefore separable by density in commercially available devices. This stripping may be done in a variety of ways, such as:
  Applying a hot hydrogen or nitrogen strip of the catalyst in the refiner's reactor prior to unloading the spent catalyst.
  Applying an inert gas strip of the spent catalyst after it is removed from the reactor.
  Applying an excess air strip of the spent catalyst after it is removed from the reactor.
  Applying a solvent extraction to the spent catalyst after it is removed from the reactor Regardless of the stripping method used, the objective of this step is to provide a free-flowing catalyst. A secondary objective of the stripping is to retain at least 50% of the sulfur on the catalyst.

The second step of the process is to process the stripped catalyst through a density separation process. An example of this process is air classification by individual particle density. The objective of this step is to segregate the stripped catalyst into two primary product streams; a lower density, lower vanadium product and a higher density, higher vanadium product.

The third step of this process is to return the lower density product for reuse in the hydroprocessing operation. The higher-vanadium product may then go directly to a metal reclamation facility.

The fourth step of this process is to purify the alumina in the higher-vanadium product after recovery of the vanadium.

An exemplary method for recovering reusable catalyst from a hydroprocessing operation may comprise: washing a granular, vanadium- and oil-contaminated, alumina-based catalyst with an oil-dissolving solvent sufficiently to render the catalyst free-flowing [non-sticky]; separating the washed catalyst into a first, higher density portion and a second, lower density portion; and returning the second, lower density portion to the hydroprocessing operation.

Alternatively, a process according to the invention may be applied to spent alumina-based catalyst materials as a way to not only recover the catalytic metals but also the alumina. Until now, the spent catalyst was heated/oxidized at high temperature to burn off carbon and sulphur etc. leaving an oxidized matrix that could be attacked by acid digestion. The heated catalyst was often heated with soda ash to render the catalytic metals soluble in a water wash as well as in acid. The complication with this process is that the alumina content is rendered almost insoluble.

A solvent wash of spent catalyst may be used to remove leftover oil content and then a simple grinding process may be used to produce a slurry. Acid digestion of this material substantially dissolves everything including the alumina and the selective separation processes disclosed above may be used to extract the various components of the spent catalyst including alumina. The value of the recovered alumina makes this process economically viable.

Some carbon and sulphur may still remain in the solvent-washed and dried spent catalyst after acid digestion for metal recovery. Inasmuch as the process does not heat treat the spent catalyst, all of it reacts with the digestion acid including the alumina. Carbon and sulphur do not react and remain as a black sludge after digestion. Prior art processes for catalytic metal recovery have used high-temperature oxidation/calcination to burn off the carbon and sulphur from spent catalyst (including oil wetted catalyst) leaving the solids carbon-, oil-, and sulphur-free and with all the catalytic metals as oxides. This makes for a reasonably clean and simple selective extraction of the catalytic metals using acid digestion. However, the calcined alumina substrate support of the spent catalyst does not react readily with the digestion acid and remains as a solid sludge that is typically eventually melted in a furnace to give a useless slag that must be sent (at a cost) for waste disposal as an inert solid.

Although particular embodiments of the present invention have been described, they are not intended to limit what this patent covers. One skilled in the art will understand that various changes and modifications may be made without departing from the scope of the present invention as literally and equivalently covered by the following claims.

What is claimed is:

1. A process for purifying alumina contaminated with iron-, titanium-, and magnesium-containing compounds comprising:
  digesting the contaminated alumina in sulfuric acid to produce a first solution comprising aluminum sulfate, ferric sulfate, titanyl sulfate, and magnesium sulfate;
  passing the first solution over metallic iron to reduce any ferric sulfate to ferrous sulfate and produce a second solution;
  adding ammonia to the second solution to precipitate hydrated titania from any titanyl sulfate;
  filtering the second solution to remove any hydrated titania and produce a third solution;
  adding ammonium sulfate to the third solution to form a fourth solution comprising ferrous ammonium sulfate and ammonium aluminum sulfate;
  crystalizing ammonium aluminum sulfate from the fourth solution;
  dissolving the crystalized ammonium aluminum sulfate to form a fifth solution;
  adding ammonium bicarbonate to the fifth solution to precipitate basic ammonium aluminum carbonate;
  recovering the basic ammonium aluminum carbonate;
  heating the recovered basic ammonium aluminum carbonate for a time and at a temperature sufficient to produce alumina, ammonia, and carbon dioxide;
  adding ammonia or ammonium sulfate to the fourth solution to adjust to equimolar conditions to form a sixth solution;
  adding oxalic acid to the sixth solution to form insoluble ferrous oxalate;
  filtering the fifth solution to remove any ferrous oxalate and produce a seventh solution;
  adding oxalic acid to the seventh solution to precipitate magnesium oxalate;
  recovering any magnesium oxalate from the seventh solution;
  heating the magnesium oxalate to form magnesium oxide;
  heating the ferrous oxalate to produce ferrous oxide and carbon monoxide; and
  reducing any ferrous oxide to metallic iron.

2. The process recited in claim 1 further comprising:
reacting the ammonia and carbon dioxide produced by heating the recovered basic ammonium aluminum carbonate with water to produce ammonium bicarbonate.

3. The process recited in claim 2 further comprising:
recycling the produced ammonium bicarbonate to the process by adding it to the fifth solution to precipitate basic ammonium aluminum carbonate.

4. The process recited in claim 1 further comprising:
filtering the first solution to remove silica.

5. The process recited in claim 4 wherein the filtering is performed with the temperature of the first solution at about 90 degrees Celsius.

6. The process recited in claim 1 further comprising refining the ammonium aluminum sulfate using multiple crystallizations.

7. The process recited in claim 6 wherein the multiple crystallizations are performed in chilled crystallization tanks.

8. The process recited in claim 7 further comprising:
providing heat pumps to transfer recovered cooling energy into heat needed to re-dissolve crystals between each crystallization.

9. The process recited in claim 1 further comprising:
washing the crystals of ammonium aluminum sulfate with a solution of ammonium sulfate to reduce impurity levels at the crystal surfaces.

10. The process recited in claim 1 wherein reducing the ferrous oxide to metallic iron comprises contacting the ferrous oxide with carbon monoxide.

11. The process recited in claim 10 wherein the carbon monoxide comprises carbon monoxide produced by thermal decomposition of the ferrous oxalate.

12. The process recited in claim 10 wherein the carbon monoxide consists of carbon monoxide produced by thermal decomposition of the ferrous oxalate.

13. The process recited in claim 1 wherein the metallic iron over which the first solution is passed to reduce the ferric sulfate to ferrous sulfate comprises scrap iron.

14. The process recited in claim 1 further comprising washing, drying and calcining the hydrated titania to produce anatase titania.

15. The process recited in claim 1 wherein the oxalic acid is produced by the oxidation of glucose with nitric acid.

16. The process recited in claim 15 wherein the oxidation of glucose with nitric acid produces nitric oxide which is then oxidized to nitrogen dioxide which is then absorbed in water to produce nitric acid.

17. The process recited in claim 1 wherein heating the magnesium oxalate to form magnesium oxide additionally forms carbon monoxide that is recycled to the process as a reducing agent for converting iron oxide to iron.

18. The process recited in claim 1 further comprising crystallizing ammonium sulfate produced when adding oxalic acid to the sixth solution to form insoluble ferrous oxalate.

19. The process recited in claim 18 further comprising decomposing the ammonium sulfate crystals in concentrated sulfuric acid to produce ammonia and additional sulfuric acid.

20. The process recited in claim 19 further comprising recycling the ammonia to the process.

21. A method for recovering reusable catalyst and alumina from a hydroprocessing operation comprising:
washing a granular, vanadium- and oil-contaminated, alumina-based catalyst with an oil-dissolving solvent sufficiently to render the catalyst free-flowing;
separating the washed catalyst into a first, higher density portion and a second, lower density portion;
returning the second, lower density portion to the hydroprocessing operation;
purifying alumina contaminated with iron-, titanium-, and magnesium-containing compounds in the first, higher density portion by
digesting the contaminated alumina in sulfuric acid to produce a first solution comprising aluminum sulfate, ferric sulfate, titanyl sulfate, and magnesium sulfate;
passing the first solution over metallic iron to reduce any ferric sulfate to ferrous sulfate and produce a second solution;
adding ammonia to the second solution to precipitate hydrated titania from any titanyl sulfate;
filtering the second solution to remove any hydrated titania and produce a third solution;
adding ammonium sulfate to the third solution to form a fourth solution comprising ferrous ammonium sulfate and ammonium aluminum sulfate;
crystalizing ammonium aluminum sulfate from the fourth solution;
dissolving the crystalized ammonium aluminum sulfate to form a fifth solution;
adding ammonium bicarbonate to the fifth solution to precipitate basic ammonium aluminum carbonate;
recovering the basic ammonium aluminum carbonate;
heating the recovered basic ammonium aluminum carbonate for a time and at a temperature sufficient to produce alumina, ammonia, and carbon dioxide;
adding ammonia or ammonium sulfate to the fourth solution to adjust to equimolar conditions to form a sixth solution;
adding oxalic acid to the sixth solution to form insoluble ferrous oxalate;
filtering the fifth solution to remove any ferrous oxalate and produce a seventh solution;
adding oxalic acid to the seventh solution to precipitate magnesium oxalate;
recovering any magnesium oxalate from the seventh solution;
heating the magnesium oxalate to form magnesium oxide;
heating the ferrous oxalate to produce ferrous oxide and carbon monoxide; and
reducing any ferrous oxide to metallic iron.

* * * * *